(12) United States Patent
Haje

(10) Patent No.: US 7,175,437 B2
(45) Date of Patent: Feb. 13, 2007

(54) DENTAL BRIDGE HOLDER ALIGNMENT MECHANISM

(76) Inventor: Emad El Haje, 1800 Eye St., Suite 801, Washington, DC (US) 20006

(*) Notice: Subject to any disclaimer, the term of this patent is extended or adjusted under 35 U.S.C. 154(b) by 452 days.

(21) Appl. No.: 10/774,452

(22) Filed: Feb. 10, 2004

(65) Prior Publication Data

US 2005/0175957 A1 Aug. 11, 2005

(51) Int. Cl.
*A61C 5/04* (2006.01)
(52) U.S. Cl. .................. 433/225; 433/34; 433/191; 433/195
(58) Field of Classification Search ............... 433/72, 433/74, 34, 215, 225, 195, 191–194
See application file for complete search history.

(56) References Cited

U.S. PATENT DOCUMENTS

| | | | | |
|---|---|---|---|---|
| 445,231 A * | 1/1891 | Page et al. | ................. | 433/211 |
| 1,122,979 A * | 12/1914 | Morgan | ................. | 433/193 |
| 1,397,192 A * | 11/1921 | Williams | ................. | 433/192 |
| 2,356,447 A * | 8/1944 | Cline | ................. | 425/11 |
| 2,471,501 A * | 5/1949 | Steigleman | ................. | 156/94 |
| 2,742,700 A * | 4/1956 | Ramsperger | ................. | 433/211 |
| 3,153,282 A * | 10/1964 | Brewer | ................. | 433/68 |
| 3,896,548 A * | 7/1975 | Zahn | ................. | 433/74 |
| 4,195,047 A * | 3/1980 | Drennan et al. | ................. | 264/17 |
| 4,270,904 A * | 6/1981 | Bogaert | ................. | 433/167 |
| 4,276,027 A * | 6/1981 | Lustig | ................. | 433/225 |
| 4,865,546 A * | 9/1989 | Naylor | ................. | 433/213 |
| 5,634,792 A * | 6/1997 | Brisendine | ................. | 433/180 |

* cited by examiner

*Primary Examiner*—Ralph A. Lewis
(74) *Attorney, Agent, or Firm*—Barnes & Thornburg LLP

(57) ABSTRACT

A positioning aid, formed T-shaped, is adhesively attached to portions of a broken denture plate prior to placement of the dental plate portions into a dental impression tray whereby the positioning aids extend into and are embedded into the impression material in the dental tray and act as positioners and stabilizers to properly align and hold the dental plate portions while the dental impression material hardens.

20 Claims, 1 Drawing Sheet

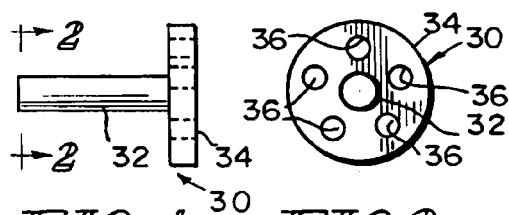
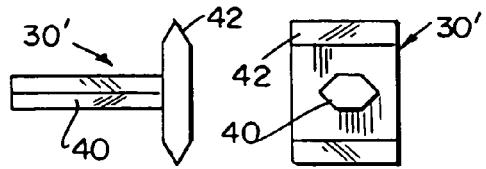
FIG. 1  FIG. 2  FIG. 3  FIG. 4
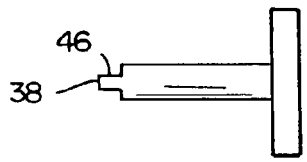
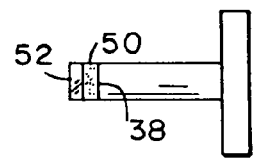
FIG. 5  FIG. 6
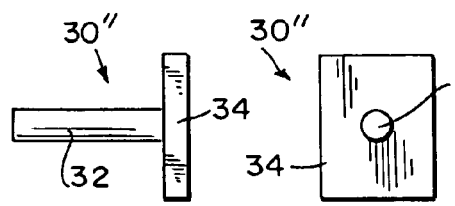
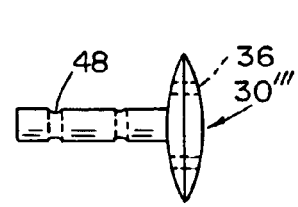
FIG. 7  FIG. 8  FIG. 9  FIG. 10
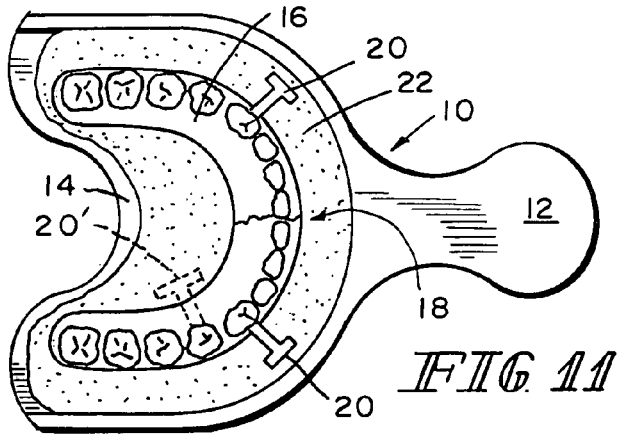
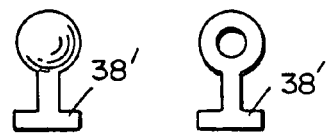
FIG. 11  FIG. 12  FIG. 13
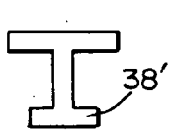
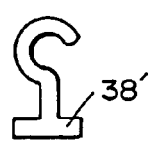
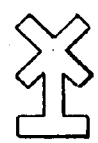
FIG. 14  FIG. 15  FIG. 16

DENTAL BRIDGE HOLDER ALIGNMENT MECHANISM

This invention relates to a system to secure or retain broken denture parts, copings, crowns and bridges on any dental device together during compression making, thus reducing the chances for misalignment or movement of the parts during the impression pick-up procedure.

BACKGROUND AND SUMMARY

Current dental practices allows a dentist to create a partial or full denture to replace missing teeth in a patient's mouth. These created dentures need to accurately replicate the teeth which they replace both for appearance and securement purposes.

To create dentures, a pliable moldable impression material is utilized to form a three-dimensional negative likeness (reverse copy) of the surface of the imprint of a patient's teeth and adjacent jaw and mouth structure. A dental technician uses this likeness as a mold form to create the denture. In the process to create the likeness, the pliable, moldable impression material (while soft) is placed in a dental impression tray. The tray with the material is inserted into a patient's mouth and pressed against a jaw and adjacent teeth (if any) of the patient wherein the impression material is displaced around the jaw to create the three dimensional negative reproduction of the patient's jaw area. The tray acts to confine the pliable material to insure that an accurate three-dimensional mold of the patient's mouth is obtained. The pliable impression material begins to set and when stiff enough, the impression tray with its stiffened impression material is withdrawn from the patient's jaw. The stiffened material thus provides an accurate three dimensional reproduction of a patient's mouth, which (after complete stiffening) can be used as a mold by a dental technician for creating crowns, implants or replacement partial or full dentures for a patient. Of necessity, accuracy in recreating the details of a patient's mouth is most important both for appearance, fit and securement. An inaccurate reproduction can look bad, can apply pressure unequally on a patient's jaw which can cause soreness and wobble affecting the fit and usability of a denture crowns or implants. Thus, the impression material must provide an accurate three-dimensional negative likeness of the patient's jaw area by clearly indicating the spatial relationships of the alvelor ridge and adjacent dentition of a patient's jaw.

When long span dental bridges are constructed, metal structure of the bridge may not provide an accurate fit, even with accurate impressions. This can cause rocking of the bridge. Often the bridge is sectioned (separated into parts) to permit a more accurate fit to alleviate magnified cantilever movements of portions of the bridge due to the metal structure. Once sectioned a new impression of the sectioned bridge is obtained and used to create a correctly fitting single piece denture bridge. An accurate pickup of section pieces is required to adequately solder the parts to obtain an accurate fit.

Denture plates are brittle and can be broken when a person with false teeth bites against something hard such as candy. To avoid recreation of a broken plate, by the normal taking of jaw impressions with the subsequent creation of a new plate, dentists can utilize the broken plate itself for the creation of the impression. Utilization of the dental plate for impressions, is a more patient friendly procedure. Some patients have little patience for the taking of impressions and actually gag when the dental impression tray with impression material is inserted into their mouths.

Utilizing of patient's broken dental plate for the taking of the impression saves patients time (they need only drop off their broken denture at the dentist) as well as impression procedures discomfort. Additionally, the dentist can better schedule his time, since he can utilize spare or fill-in time during the day to create the replacement dental plate. The pieces of the broken dental plate or bridge are placed into patient's mouth and then a tray containing the impression material is placed over them to create an accurate three-dimensional likeness similarly as done with a patient's mouth. A positional problem occurs when utilizing broken plate pieces to recreate the necessary unitary structure in the dental impression tray. The broken pieces have to be positioned and aligned exactly to recreate the unbroken original. Setting broken pieces onto the impression tray and retaining them in contact and proper alignment is difficult. This procedure is very technique sensitive and unforgiving to any movement of the pieces, since the pliable impression material when forced around the pieces can cause the pieces to move.

The instant invention provides for the secure attachment of positional aids onto the broken dental plate pieces prior to insertion of the dental plate pieces into the impression tray filled with the pliable impression material. The positional aids stick outwardly from the dental plate pieces and act as levers or paddles whereby the dentist by pressing on the positional aid or on the impressional material can move the dental plate pieces into proper alignment. The positional aids help to hold the dental plate pieces while the impression material hardens to form a proper mold for recreating a new dental plate. Thus, the aids act to provide a tool for obtaining the desired complete and accurate three-dimensional creation of the patient's denture.

Other objects, advantages and novel features of the present invention will become apparent from the following detailed description of the invention when considered in conjunction with the accompanying drawings.

BRIEF DESCRIPTION OF THE DRAWINGS

FIG. 1 shows a side elevation view of a dental aid,

FIG. 2 shows an end view of the dental aid of FIG. 1 taken on the line 2—2 of FIG. 1, FIGS. 3 and 4 are similar to FIGS. 1 and 2, but show a modification of the dental aid of FIGS. 1 and 2 wherein the shape of the dental aid varies from the circular cross section of FIGS. 1 and 2, FIG. 5 shows a modification of the dental aid wherein there is a necked down end on the dental aid, FIG. 6 shows a modification of the dental aid wherein an adhesive surface is attached to the end of the dental aid, FIGS. 7 and 8 are similar to FIGS. 1 and 2 but show a variant in the shape of the outer end of the dental aid, FIGS. 9 and 10 are similar to FIGS. 1 and 2 but show a variant to the cross-sectional shape of the dental aid;

FIG. 11 shows how the dental plate pieces and dental aids are placed into a dental impression tray; and FIGS. 12–16 are similar to FIGS. 7 and 8, but show further variants to the shape of the head and foot portions of the outer and inner ends of the dental aid.

DETAILED DESCRIPTION OF THE DRAWINGS

FIG. 11 shows a dental impression tray 10 with a handle portion 12 and a recessed portion 14 into which a layer of dental impression material 22 such as ALGINATE or IMPERGOM is placed. A dental plate 16, broken in two pieces along fissure line 18. is shown in the dental impression in tray 10. The initial filling of dental impression material does not cover the plate 16 so the dentist can view and insure proper alignment of the pieces. Adhesively attached to outside facing portions of the dental place 16 are positional aids 20. Internally facing aids 20$^1$ can also be adhesively attached to the dental plate 16. The two portions of the dental plate are properly aligned by pushing on the positioning aids 20 or pushing on the dental impression material 22 adjacent the positioned aids 20. Pushing on the material 22 adjacent an aid 20 causes movement of the aid 20 to assist in aligning the broken pieces of the dental plate 16. After proper alignment is obtained, the cavity is filled with more dental impression material to completely cover the broken denture and the material is allowed to harden. The hardened material will then form a cast of the outer surface of the broken denture upon removal from the impression tray 10. Inversion of the hardened cast and broken denture 16 will provide an underside casting area for making an impression of a patient's gum line under the denture. This area can be filled with dental impression material, which can then harden. Thus, the dentist will have an upper and lower cast of the patient's broken denture and a replacement denture can be made.

FIGS. 1 and 2 show a dental aid 30 having a elongated peg portion 32 of rounded cross-section and a rounded enlarged head end portion 34. The pegs can be made of plastic, ceramic or metal. Ideally the pegs will have the same coefficient of thermal expansion as the impression material. A plurality of holes 36 are created in the head portion to permit the dental impression material to pass through (while soft) to help secure the portion of the aid in the impression tray 10 (FIG. 11). The end 38 of the peg portion is adhesively or otherwise attached to the broken dental plate pieces 16 prior to insertion of the divided plate pieces into the partial filled dental impression tray 10.

As explained supra, after insertion into the partially filled tray, the dentist can properly align the dental plate pieces by pushing or pulling (in an appropriate direction) the dental aids 30. Because the aids rest in dental impression material, there is resistance to their movement and release of the aids will cause them to retain their adjusted position due to the gooey texture of the unhardened dental impression material. As the peg portions 32 of the aids are long, they act as levers on the dental plate 16 for ease in alignment of the dental plate 16 pieces. By having holes 36 in the enlarged portion 34, the dental impression material can flow into the holes 36 to help hold the dental aid in a fixed secure position in the dental tray 10.

FIGS. 3 and 4 show a dental aid 30$^1$ wherein the cross-section of the elongated peg portion and the enlarged head portion is substantially rectangular with tapered ends 40–42 as opposed to the rounded configuration of FIGS. 1 and 2. The taper assists in the initial insertion of the dental plates 16 into the partially filled dental impression tray 10. The enlarged end portions could also be provided with holes similar to the holes 36 of FIGS. 1 and 2.

FIGS. 7 and 8 show a position aid 30" with a circular cross-section in the peg portion 32 and a rectangular cross-section for the enlarged portion 34. FIGS. 9 and 10 show a positional aid 3$^{111}$ with airfoil cross-sections for the peg portion and the enlarged head portion and holes 48 in the peg portion.

FIG. 12 shows the head portion as a round ball.
FIG. 13 shows the head portion as donut shaped.
FIG. 14 shows the head portion as a rectangular bar (T-shaped).
FIG. 15 shows the head with a hook shape.
FIG. 16 shows the head with a star or "X" shape.
Each of the FIGS. 12–16 also provide a wider glue end 38' to ensure a better attachment.

Any combination of the cross-section configurations shown can be utilized as well as any configuration with or without holes 36 and 48. Likewise, the number and location of holes 36 and 48 can be varied. FIG. 5 shows having the end 38 of the peg portion necked-down at 46 to facilitate breaking or as to provide for easier release of the dental plate 16 from the cast.

FIG. 6 shows equipping the end of the peg portion 32 with an a adhesive pad 50 covered with an easy released paper 52 or soluble material for access to the adhesive pad 50 for attachment of the dental aid 10, 10', 10$^{II}$, 10$^{III}$ to the denture plate 16. Alternatively a dentist could use SUPER GLUE or some other fast drying and strong adhesive for attachment of the dental aid to a dental plate 16.

Although the present invention has been described and illustrated in detail, it is to be clearly understood that the same is by way of illustration and example only, and is not to be taken by way of limitation. The spirit and scope of the present invention are to be limited only by the terms of the appended claims.

What is claimed:

1. A system for repairing broken dental plates by creating a new dental impression form from existing dental plate pieces comprising:
    creating elongated pegs with a narrow cross-sectional area at one end and an enlarged portion at another end;
    adhesively attaching the narrow cross-sectional area of at least one peg to each dental plate piece and with the enlarged portion extending beyond an edge of each dental plate piece;
    inserting each dental plate piece with its at least one attached peg into a dental impression material that has been layered into a impression tray;
    aligning the inserted dental plate pieces into a proper alignment by applying pressure to the enlarged portions of the attached elongated pegs to cause proper movement of the pegs attached to the dental plate piece with respect to another dental plate piece in the impression tray; and
    subsequently hardening the impression material to create a new mold form for the dental plate pieces.

2. The system of claim 1 wherein the enlarged portion is created as a elongated thin member with a width in excess of its thickness.

3. The system of claim 2 wherein the positioned aid is created from a material with a thermal expansion similar to that of the impression material used to create the dental plate impression.

4. The system of claim 3 wherein the enlarged portion is created with apertures therein.

5. The system of claim 3 wherein the enlarged portion is created with tapered edges.

6. The system of claim 3 wherein the elongated peg is created with apertures.

7. The system of claim 2 wherein the enlarged portion is created with apertures therein.

8. The system of claim 7 wherein the elongated peg is created with apertures.

9. The system of claim 2 wherein the enlarged portion is created with tapered edges.

10. The system of claim 2 wherein the elongated peg is created with apertures.

11. The system of claim 1 wherein the positioned aid is created from a material with a thermal expansion similar to that of the impression material used to create the dental plate impression.

12. The system of claim 11 wherein the enlarged portion is created with apertures therein.

13. The system of claim 11 wherein the enlarged portion is created with tapered edges.

14. The system of claim 11 wherein the elongated peg is created with apertures.

15. The system of claim 1 wherein the enlarged portion is created with apertures therein.

16. The system of claim 15 wherein the enlarged portion is created with tapered edges.

17. The system of claim 15 wherein the elongated peg is created with apertures.

18. The system of claim 1 wherein the enlarged portion is created with tapered edges.

19. The system of claim 1 wherein the elongated peg is created with apertures.

20. The system of claim 1 wherein additional impression material is added to the impression tray prior to the hardening step.

* * * * *